United States Patent
Adato et al.

(10) Patent No.: US 10,282,833 B2
(45) Date of Patent: May 7, 2019

(54) GATE-LEVEL MAPPING OF INTEGRATED CIRCUITS USING MULTI-SPECTRAL IMAGING

(71) Applicant: Trustees of Boston University, Boston, MA (US)

(72) Inventors: Ronen Adato, Boston, MA (US); Ajay Joshi, Lexington, MA (US); M. Selim Unlu, Newton, MA (US); Bennett B. Goldberg, Chicago, IL (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 15/771,493

(22) PCT Filed: Nov. 30, 2016

(86) PCT No.: PCT/US2016/064109
§ 371 (c)(1),
(2) Date: Apr. 27, 2018

(87) PCT Pub. No.: WO2017/095862
PCT Pub. Date: Jun. 8, 2017

(65) Prior Publication Data
US 2018/0350062 A1    Dec. 6, 2018

Related U.S. Application Data (60) Provisional application No. 62/260,930, filed on Nov. 30, 2015.

(51) Int. Cl.
*G01N 21/47* (2006.01)
*G06T 7/00* (2017.01)
(Continued)

(52) U.S. Cl.
CPC .......... *G06T 7/0006* (2013.01); *G01N 21/47* (2013.01); *G01N 21/956* (2013.01);
(Continued)

(58) Field of Classification Search
CPC . G01N 21/00; G01N 21/47; G01N 2021/8461
See application file for complete search history.

(56) References Cited

U.S. PATENT DOCUMENTS

| 6,883,148 B1 | 4/2005 | Teig et al. |
| 8,139,846 B2 | 3/2012 | Bajura et al. |

(Continued)

*Primary Examiner* — Jonathan M Hansen
(74) *Attorney, Agent, or Firm* — BainwoodHuang (57) ABSTRACT

Optical verification testing of an IC includes obtaining images of the IC by, for each image: (i) illuminating the IC with excitation light, wherein the excitation light corresponds to a respective specific optical excitation of a predefined spectrum of optical excitations (e.g., wavelength spectrum); and (ii) detecting scattered light from the IC in response to the specific optical excitation. For each of a set of sub-regions of the images, the respective sub-region is mapped to at least one of (i) a specific sub-unit of a predefined set of sub-units (e.g., gates) of the IC and (ii) a null result, thereby creating a representation of a detected layout of the IC as an arrangement of the sub-units. The representation can be used to verify that an as-fabricated layout is consistent with an as-designed layout, to detect unauthorized modifications of the IC structure.

12 Claims, 6 Drawing Sheets

(51) Int. Cl.
*G01N 21/956* (2006.01)
*G06F 17/50* (2006.01)

(52) U.S. Cl.
CPC ........ *G06F 17/5081* (2013.01); *G06T 7/0002* (2013.01); *G06T 7/0004* (2013.01); *G06T 2207/10152* (2013.01); *G06T 2207/20021* (2013.01); *G06T 2207/20076* (2013.01); *G06T 2207/20081* (2013.01); *G06T 2207/30148* (2013.01)

(56) References Cited

U.S. PATENT DOCUMENTS

| | | |
|---|---|---|
| 8,154,308 B2 | 4/2012 | Kormanyos |
| 8,242,793 B2 | 8/2012 | Kumhyr et al. |
| 9,129,715 B2 * | 9/2015 | Adler .................. G21K 7/00 |
| 2002/0073388 A1 | 6/2002 | Orshansky et al. |
| 2005/0135738 A1 | 6/2005 | Shin et al. |
| 2009/0100392 A1 * | 4/2009 | Ivaldi .................. G03B 27/52 |
| | | 716/106 |
| 2011/0280468 A1 * | 11/2011 | Song .................. G01R 31/311 |
| | | 382/147 |
| 2013/0024827 A1 | 1/2013 | McIlrath |
| 2013/0148194 A1 | 6/2013 | Altug et al. |

\* cited by examiner

GATE-LEVEL MAPPING OF INTEGRATED CIRCUITS USING MULTI-SPECTRAL IMAGING

STATEMENT OF GOVERNMENT SUPPORT

This invention was made with Government Support under Contract No. W911NF-12-R-0012 awarded by the Army Research Office and Contract No. 1526533 awarded by the National Science Foundation. The Government has certain rights in the invention.

BACKGROUND

The invention is related to the field of integrated circuit verification testing.

SUMMARY

Techniques are disclosed for testing whether the layout of an integrated circuit (IC) as manufactured is consistent with the as-designed layout. The advantages of the techniques may be significant due to the high degree of complexity and outsourcing in the modern IC supply chain. Currently the majority of chip designers are 'fabless' and outsource the fabrication of their circuits to dedicated foundries. There is a severe emerging threat that circuitry can be modified or added as chip layouts pass through multiple parties during the design and fabrication stages. Such modifications are challenging to prevent and test for and can perform malicious functions such as subverting firewalls, leaking sensitive information or compromising device functionality (e.g. reducing the security of encryption).

Also disclosed are testing techniques based on use of "nanoantenna labels", which could be used in conjunction with the disclosed gate-level mapping techniques in some embodiments.

TECHNICAL BACKGROUND

Digital integrated circuits (ICs) are physical devices that perform complex digital logic operations. Layout diagrams of example simple digital logic circuits with a small number of logic gates are shown below. A physical electronic device that performs functionality specified by a logic diagram consists of a series of interconnected transistors and input/output terminals where voltages can be applied and read out.

In modern ICs these transistors and wires are fabricated in a series of layers on silicon substrates using advanced lithographic processes. Typical ICs contain on the order of $10^6$-$10^9$ transistors and logic gates. Because of their immense complexity, modern ICs are essentially never designed transistor by transistor. Instead they are built up in a modular fashion that follows the concept of logic diagrams. The physical transistors and connections that form each logic gate are grouped together in standard cells that are saved in a library. Gates are physically realized by the layout of metal lines and tungsten contacts among transistors. In a step in the design process of ICs (place and route) a large logic diagram is converted to a physical CAD layout by matching each gate to its corresponding standard cell, placing it somewhere on the chip layout and connecting it to other cells. The process of arranging and connecting the various standard cells is complex and generally accomplished using automated computer algorithms that optimize based on considerations such as the physical area used as well as e.g. the time it takes for signals to propagate through the circuit.

Techniques are disclosed for identifying the physical standard cells in an IC based on the way they reflect light at different optical wavelengths and polarizations. The method dramatically reduces the required optical resolution and pixel count needed to obtain a map of the IC layout.

Considering the current trend toward separation of IC design expertise and IC fabrication expertise, and the fact that the disclosed technologies have both design and test aspects, there several commercialization options that are possible. Customers could be provided with software tools (IC design software) that allow them to implement the techniques. These products might take the form of a stand-alone software package or one that is integrated into widely used IC design and simulation software. These could be provided directly to chip designers or to foundries who could effectively sell 'security' in this manner. The technique could also be provided as a service. Alternatively the hardware and processing algorithms required to test devices could be sold, licensed or used by a dedicated test company. In addition to tampering detection, there are possible applications to detecting defects, counterfeiting and intellectual property theft.

Security Issues and Shortcomings of Current Approaches

Security issues have become significant as a result of the increasingly complex, fragmented and global multi-stage process by which ICs are produced. This trend has opened the door for numerous security threats including piracy, counterfeiting and malicious tampering. Malicious tampering is manifest by the insertion of a few rogue gates into an IC in order to, for example, subvert firewalls, leak sensitive information or compromise device functionality. In analogy with the software threats, these may be termed Hardware Trojans. Unlike software vulnerabilities, Hardware Trojans require highly specialized equipment and expertise to detect and cannot simply be patched in the field. Efforts by the U.S. Defense Department to control the full process for fabricating its chips in the Trusted Foundry program and the large body of research on possible modifications to the chip design and fabrication flow highlight the significance of this problem as well as the lack of appropriate testing solutions.

Current electronic testing methods fall short in testing for Hardware Trojans. Digital tests cannot exhaustively sample the massive state space which scales nonlinearly with IC complexity, and analog measurements are highly sensitive to minor fabrication variations. Both can be readily designed around by an adversary. There is therefore a clear and pressing need for tools that enable direct, rapid and low cost detection of IC tampering.

Any change in the functionality of an IC must map to a change the physical structures that define its logic. A direct image of the layout therefore offers the most direct and exhaustive route to detect tampering. Measuring the physical structures as opposed to the electrical signals produced by an IC is fundamentally advantageous. Electronic measurements must consider and be designed to be robust over a wide range of complex activation and action characteristics of Hardware Trojans, in contrast to direct IC layout images that do not. Spatial mapping also has more favorable scaling rules since the measurement space varies only linearly with transistor or gate count. Traditional imaging methods, however, are fundamentally limited in their ability to handle the enormous range in length scales that are present in modern ICs. The physical features that define the transistors and their associated interconnects have dimensions below 100 nm, yet billions of them together cover an area on the order of cm2. From the standpoint of the optical resolution, these dimensions are at the limits of what can be achieved with solid immersion lenses (SILs) at the near-infrared (IR) wavelengths (1-3 um) that are required to optically access IC circuitry through the silicon (Si) substrate. The extremely high numerical apertures (NA) required, however, sacrifice field of view and thus present significant challenges to imaging over large areas. A similar bottleneck exists in terms of the number of spatial samples that would be required to image a full IC at a discretization commensurate with the smallest feature sizes, which are about 10-100 nm. To simply record this many image points (pixels) with a conventional laser scanning confocal microscope would require at least several hours to tens of days.

BRIEF SUMMARY

A multi-spectral imaging approach is used that takes advantage of the inherent modularity of IC design. The approach use of the fact that structural information is encoded in the spectral domain to dramatically relax traditional constraints related to resolution and sampling throughput in an imaging system. In contrast to traditional spectroscopy techniques seeking to obtain new chemical or material property information, the disclosed approach utilizes spectral scattering and pattern recognition as optical design tools to reduce the required optical resolution and spatial sampling rate by several orders of magnitude. This enables the possibility of mapping the type and location of every logical gate in an IC in a short period of time (e.g., minutes) using a modest imaging system.

The disclosed techniques enable rapid validation of the layout of an IC to detect any unauthorized modification. Relevant competing technologies are: (i) reverse engineering; (ii) electronic logic testing; (iii) electronic side-channel analysis and; (iv) traditional backside imaging.

In comparison with known prior techniques, the disclosed methods are non-destructive and measure the physical IC layout as opposed to electronic signals. This is a more direct test of modifications. As such the disclosed techniques cannot be defeated by circuit design techniques such as triggering on rare events or established methods of reducing side channel (e.g. leakage power, delay) signatures. They provide high detection rates without the need to consider test-vector generation or controlling for noise introduced in electronic signals by fabrication variations. In comparison with (iv) the disclosed techniques enable accurate testing at far lower optical resolution and sampling rates, which translate to dramatic improvements in simplicity of the required instrumentation, ability to scale with shrinking sizes of IC features and throughput (speed at which an IC can be tested).

Thus, disclosed is optical verification testing of an integrated circuit includes obtaining images of the integrated circuit by, for each image: (i) illuminating the integrated circuit with excitation light, wherein the excitation light corresponds to a respective specific optical excitation of a predefined spectrum of optical excitations (e.g., wavelength spectrum); and (ii) detecting scattered light from the integrated circuit in response to the specific optical excitation. For each of a set of sub-regions of the images, the respective sub-region is mapped to at least one of (i) a specific sub-unit of a predefined set of sub-units (e.g., gates) of the integrated circuit and (ii) a null result, based on an intensity of one or more pixels within the sub-regions of the one or more images, wherein for each image, the intensity of the pixels corresponds to an intensity of detected scattered light from a corresponding region of the portion of the integrated circuit in response to the respective specific optical excitation, thereby creating a representation of a detected layout of the integrated circuit as an arrangement of the sub-units. The representation can be used to verify that an as-fabricated layout is consistent with an as-designed layout, to detect unauthorized modifications of the IC structure.

In one embodiment, illuminating the integrated circuit includes using a broadband optical source generating broadband illumination across the spectrum of optical excitations, and wherein detecting scattered light from the integrated circuit includes using filters for detecting respective responses to the optical excitations occurring simultaneously in response to the broadband illumination. Alternatively, in another embodiment, illuminating the integrated circuit includes using a series of narrowband sources each providing a corresponding distinct one of the optical excitations, and wherein detecting scattered light from the integrated circuit includes multiple distinct detections each occurring when a corresponding distinct optical excitation is provided.

In one embodiment, the predefined spectrum of optical excitations includes a wavelength spectrum. It may further include a set of polarizations used in combination with wavelengths of the wavelength spectrum. Alternatively, the set of polarizations may be used independently of any set of wavelengths.

In one embodiment, mapping the sub-regions includes use of a machine learning technique. The machine learning technique may be a training-based Bayesian technique providing estimates of probabilities used to map the sub-regions to respective sub-units.

In one embodiment, the predefined set of sub-units are gates.

In one embodiment, the predefined set of sub-units are antenna-labeled versions of a corresponding set of non-labeled sub-units from which the antenna-labeled version are created by addition of antenna structure for enhancing distinctness of optical response.

In one embodiment, the method is used in verifying a detected layout of a fabricated integrated circuit to a designed layout for a design of the fabricated integrated circuit, and further including comparing the representation of the detected layout to a separate representation of the designed layout to detect deviation of the detected layout from the designed layout.

In another aspect, disclosed is an integrated circuit having a plurality of antenna-labelled sub-units being antenna-labeled versions of a corresponding set of non-labeled sub-units from which the antenna-labeled version are created by addition of antenna structure for enhancing distinctness of optical response. Such an integrated circuit may be the subject of verification testing as described and claimed herein.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

DETAILED DESCRIPTION

Figure 1:
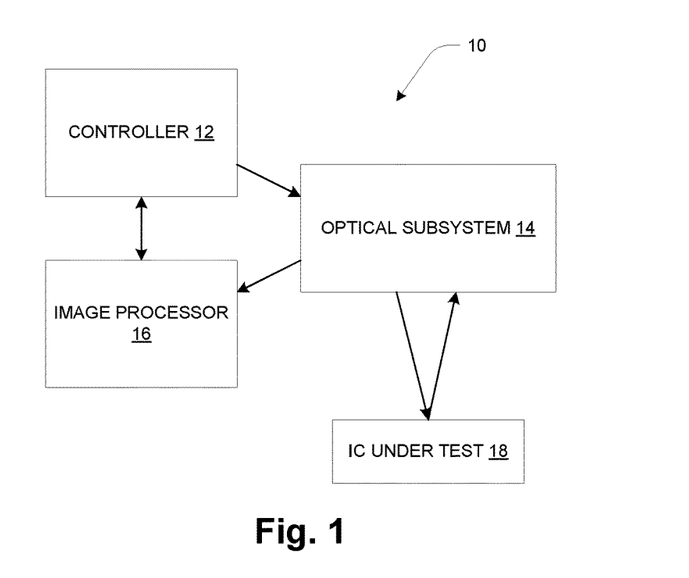
FIG. 1 is a block diagram of an optical verification testing system.

FIG. 1 shows a testing system 10 including a controller 12, optical subsystem 14, and image processor 16. Under control of the controller 12, the optical subsystem directs optical illumination to an integrated circuit (IC) under test 18 and receives reflected optical energy in response. As described more below, the test system 10 uses a "multi-spectral" approach in which images are obtained from the IC under test 18 for different optical excitations, e.g., illumination at different wavelengths, polarizations, etc. For each optical excitation, the pattern of reflected optical energy is scanned and converted into an electronic representation of a corresponding image of the IC under test 18. These images are processed by the image processor 16, under control of the controller 12, to construct a representation the layout of the IC under test 18.

Figure 2:
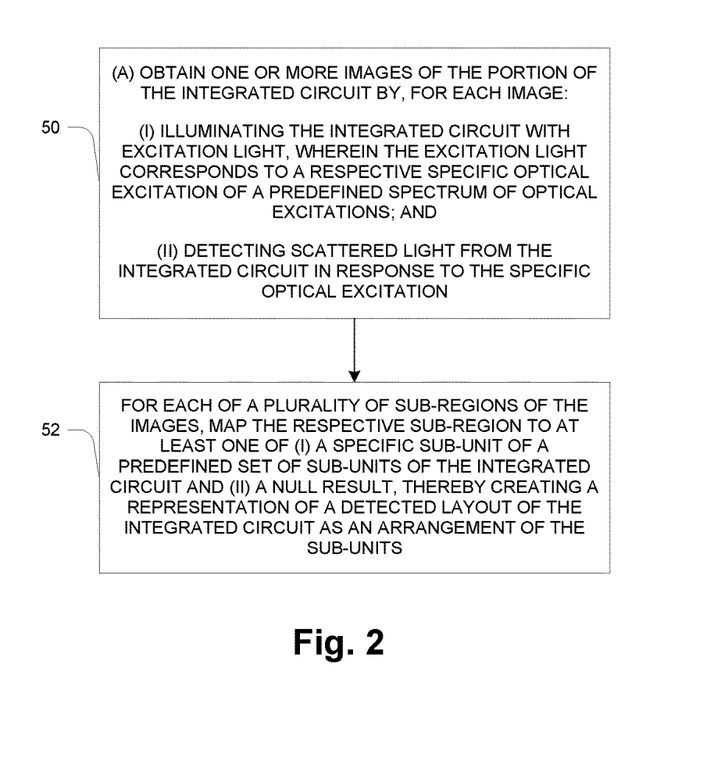
FIG. 2 is a flow diagram of high-level operation.

FIG. 2 describes aspects of operation, namely optical verification testing of a portion of an IC (e.g., IC under test 18). At 50, the system 10 obtains one or more images of the portion of the integrated circuit. The following are performed for each image:

(i) illuminating the integrated circuit with excitation light, wherein the excitation light corresponds to a respective specific optical excitation of a predefined spectrum of optical excitations; and (ii) detecting scattered light from the integrated circuit in response to the specific optical excitation.

At 52, for each of a plurality of sub-regions of the images, the respective sub-region is mapped to at least one of (i) a specific sub-unit of a predefined set of sub-units of the integrated circuit (e.g., a specific gate of a set of predefined gates) and (ii) a null result, thereby creating a representation of a detected layout of the integrated circuit as an arrangement of the sub-units. "Null result" refers to the situation in which no suitable mapping for a sub-region can be made. The mapping is based on an intensity of one or more pixels within the sub-regions of the one or more images, wherein for each image, the intensity of the pixels corresponds to an intensity of detected scattered light from a corresponding region of the portion of the integrated circuit in response to the respective specific optical excitation.

Figure 3:
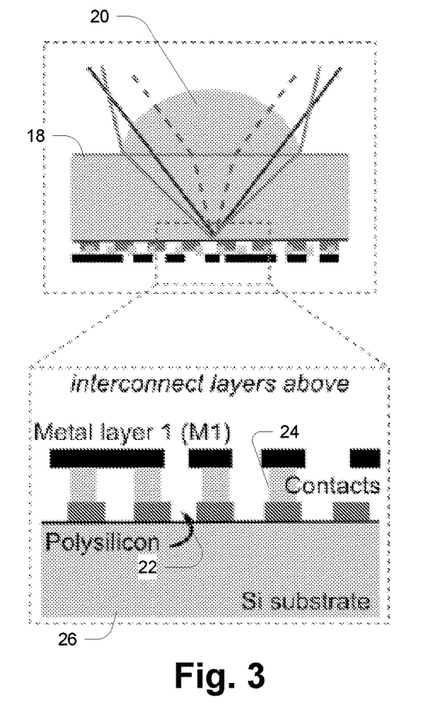
FIG. 3 is a schematic diagram of backside imaging and structure of an IC.

FIG. 3 shows certain details of IC backside imaging which is used in one embodiment. At 20 is a SIL or other type of numeric aperture increasing lens (NAIL), which is part of the optical subsystem 14. Certain details of the IC 18 are shown at bottom, specifically metal layer 1 (M1), polysilicon 22, and contacts 24, arranged on a silicon (Si) substrate 26. The representation at bottom shows the IC flipped vertically from its orientation in the upper part of the figure.

Figure 4:
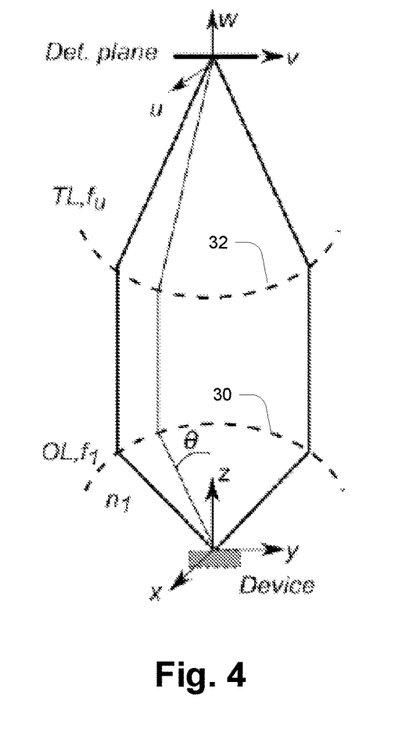
FIG. 4 is a schematic diagram of optical aspects of the system.

FIG. 4 is a generalized depiction of an image forming system and coordinates along with detail of backside imaging geometries. Gaussian reference spheres for the objective (OL) and tube (TL) lenses are shown as dashed curves 30, 32 in the diagram. Reference coordinate systems are also shown.

Gate-level Mapping of Integrated Circuits

Integrated circuits consist of a layered stack built up over a Si substrate. The bottom-most layers define an active region containing the transistors and comprise doped regions in the Si and polysilicon. The first metal layer (M1) typically is used to connect combinations of these transistors to form standard logic gates. Imaging these basic structures would provide an ideal means with which to directly verify faithful fabrication of an as-designed chip layout at an untrusted foundry. However, such an approach would require tremendous resolution and throughput.

Such obstacles are addressed by taking advantage of inherent modular nature of IC circuit layouts in conjunction with a spectroscopic approach. The concept is based on the fact that the metal structures that determine the gate level connections, such as those in 3, are not free to take on any arbitrary geometry. Instead they must define one of a series of standard physical representations of the various digital logic gates used to implement the functionality of the IC. Examples of such gates are described below. Their physical dimensions are generally more than an order of magnitude larger than the smallest features in the IC. The gates in a current 45 nm process have linear dimensions on the order of 1 mm. The micron-scale gates are defined as the smallest spatial unit to be imaged, as opposed to the much smaller individual wires and transistors that make up the gates, which can dramatically relax resolution and sampling rate requirements. Optical resolution on the order of 1 mm can easily be achieved even without a SIL/NAIL. Sampling at this rate such that approximately one gate maps to one pixel reduces the required pixel count by 2-4 orders of magnitude compared over an approach that images smaller features. This implies the ability to image a full chip (cm$^2$ area) in minutes at current image data acquisition rates.

The disclosed technique seeks to identify gates on the basis of their response to light incident at different excitations, such as wavelengths and polarizations. This response is referred to as spectral response hereinafter. The disclosed methods leverage the correspondence of spatial/structural information to features in the spectral domain. Each gate is therefore treated as an effective material that can be identified on the basis of such an overall spectral response. Despite being engineered explicitly for electronic as opposed to optical functionality, the sub-wavelength metallic structures that define the IC gates act as optical metamaterials, characterized by optical properties unique to their engineered structure. The pattern of optical properties provides the spectral response that is used to identify the structure.

Figure 5:
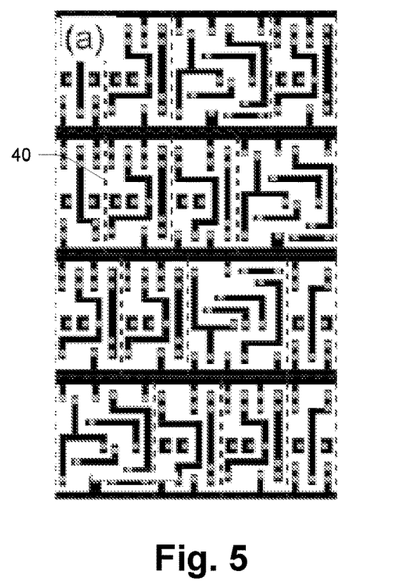
FIG. 5 is a layout diagram of logic gates in a section of an IC.
Figure 6:
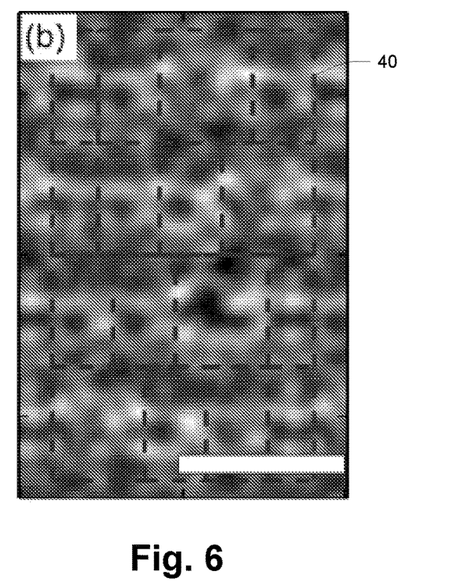
FIG. 6 is a simulated image of the layout at a given wavelength.
Figure 7:
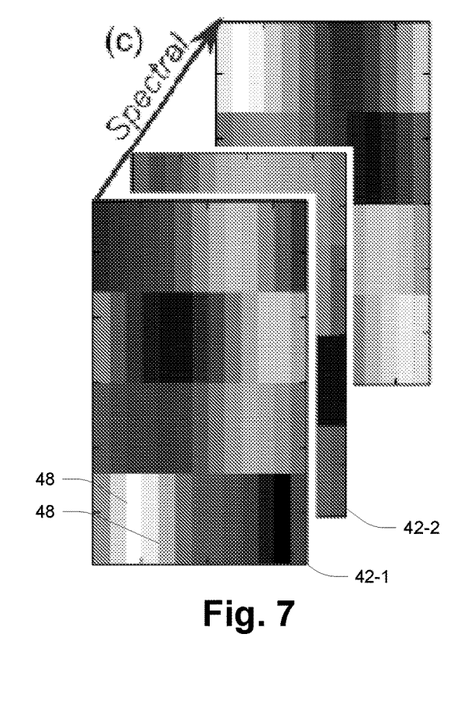
FIG. 7 is a multi-spectral set of images of the layout each corresponding to an image collected at a different wavelength-polarization combination.
Figure 8:
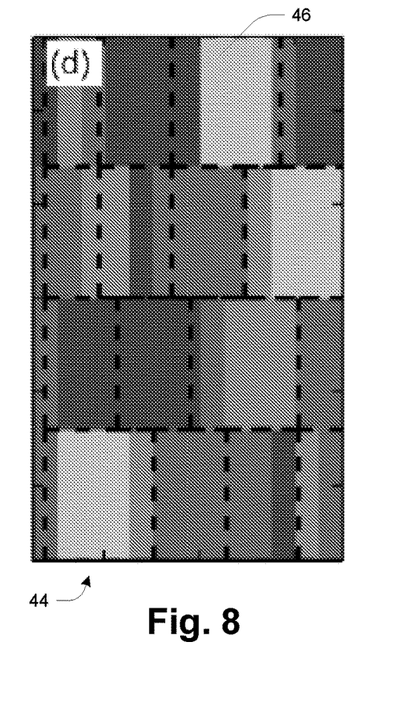
FIG. 8 is a gate map generated from the images of FIG. 7, with gate types indicated by shading.

FIG. 5-8 illustrate the multi-spectral backside imaging for rapid gate-level mapping of an integrated circuit. FIG. 5 shows a layout of a tiling of integrated circuit gates, specifically the M1 lines thereof. Dashed lines 40 indicate gate boundaries. FIG. 6 is a simulated high NA (3.4) image of the layout at a first wavelength, e.g., 1060 nm in the near infrared (NIR). The circuit is illuminated with light polarized in the y-direction. FIG. 7 shows a set of multi-spectral images 42-1,42-2, . . . , of the circuit. Such a set is also referred to as an "image stack" herein. The images are collected at low resolution (NA=0.8) and sampled at a low rate in the spatial dimension (D=250 and 1400 nm in the x and y-directions). Each panel corresponds to an image collected at a different wavelength-polarization combination. FIG. 8 shows a gate map 44 generated from the set of images of FIG. 7. Pixels 46 are shaded to indicate a gate type from among six possible gate types.

Applying established pattern recognition techniques, the image processor 16 (FIG. 1) associates each spatial pixel 48 in the image stack with a different logic gate to form the final map of FIG. 8. In comparison with the purely spatial sampling approach, these few (e.g., five) spectral measurements are dramatically more efficient than an estimated 102-104 samples that would be needed to image a 1 mm$^2$ gate with D in the range of 10-100 nm.

The disclosed approach is distinct from traditional spectroscopic techniques in that the spectral information itself is not the end goal. Instead it is utilized as an optical design tool that can circumvent traditional limits and trade-offs associated with optical resolution, sampling and throughput. The efficacy of the technique depends on the interplay between the spectral fingerprints of the IC gate objects, the method by which they are identified and the design elements of the optical system 14. The approach is demonstrated herein with reference to a test set of six fundamental two-input logic gates from the open source Nangate 45 nm library. Specific implementations with the smallest geometric footprint are chosen, and thus certain results may reflect a lower bound in terms of performance for the 45 nm process and may be indicative of an ability to scale to higher technology nodes.

Spectral Fingerprints and Classification

Figure 9:
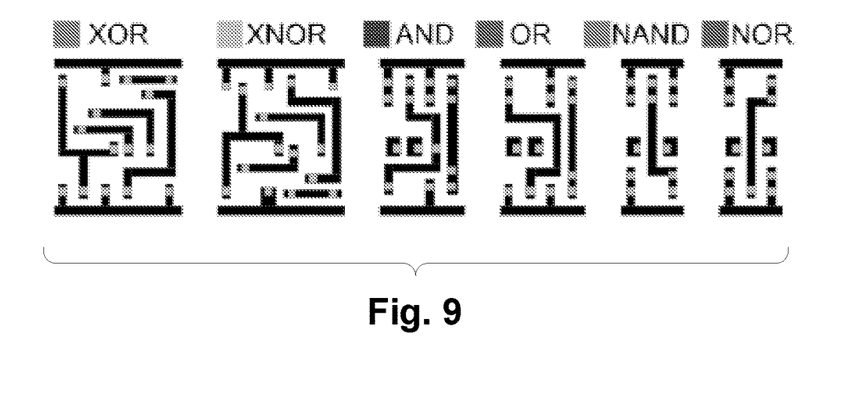
FIG. 9 is a set of schematic depictions of metal-1 layout of six gate types.
Figure 10:
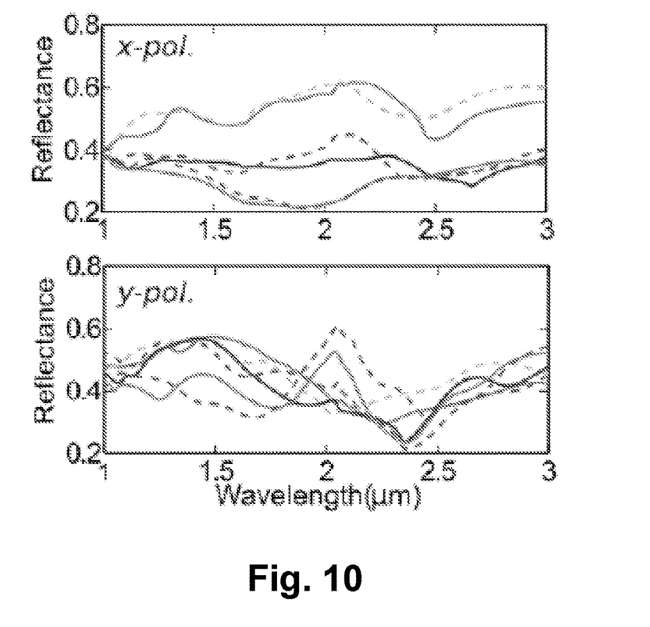
FIG. 10 is a pair of plots showing spectral response for the six gates under x-polarized and y-polarized illumination.

FIGS. 9-10 describe additional detail of spectroscopy of integrated circuit metamaterials. FIG. 9 shows schematics of metal 1 layers of the six gates (XOR, XNOR, AND, OR, NAND, and NOR). The plots of FIG. 10 show simulated spectral response for the six gates under x-polarized and y-polarized illumination.

A correspondence between spectral fingerprints of the IC gates and their substructure forms the basis of the approach. The results in the figure correspond to simplified simulations of each gate in isolation. Each of the six gates in the test set is defined by a unique series of M1 wires. When illuminated, these wavelength scale wires support current oscillations that are highly dependent on the wire geometry and the illumination wavelength and polarization. The detected signals are therefore highly unique for different gates and vary strongly as a function of wavelength and polarization of the incident field. This is evident in the reflectance spectra, as well as series of near-field current distributions (not shown). An important feature is that although the induced current distributions and far-field spectral responses are unique fingerprints of the different gates, there may be no simple one-to-one mapping between specific modes and far-field features. Instead the current modes couple to each other in a complex fashion in the near-field and produce a far-field response that is the result of coherent interference between their scattered radiation as well as the signal reflected from the Si—SiO2 interface. This motivates a statistical classification approach that is applied to distinguish between the different gates, as described more below.

A second observation is that the majority of the current distributions excited appear to correspond to higher order modes. This is important as it implies that geometry-dependent spectral features may exist over a very broad wavelength range and to persist in the near-IR for essentially any IC gate design even as dimensions are reduced at advanced technology nodes. This can be qualitatively validated by considering a simple estimate approximating the wires as Fabry-Perot resonators for current modes in accordance with common models for dipole antennas. The length scales of the M1 wires in the gates in FIG. 9 range from about 100-1500 nm. This indicates that a spectral response that is a strong function of the gate geometry can be observed at wavelengths between 0.4-9 um. This very broad range that extends far into the infrared indicates ample room for reduction in wire length before near-IR resonant structures are no longer naturally present.

To link the spectral reflectance of our gate objects to the response of an image pixel, it is assumed that the power incident at the detector has been appropriately normalized by a suitable background. A variable q indexes the polarization state such that (l;q) defines the spectral feature. The spectral reflectance, R(l;q; c), depends on the feature (l;q) and the underlying gate class, indexed by c, and gives the overall fraction of the incident power reflected and collected by the collection objective. R(l;q; c) may be assumed to account for imaging system effects such as NA and W and indeed may be calculated directly from simulated images, as described more below.

A key consideration is to determine an ideal, small set of features (li;qi) to measure. This depends directly on the elements of the optical system 14 that govern R and the range of spectral features that can be accessed. In order to address these issues, Bayes' theorem, which is the basis for an intuitive and established classification method, may be used. A spectral reflectance measurement Mi=S(li;qi)/S0 is used to identify the underlying class, c0 via the dependence on R(li;qi; c). Because of inherent measurement error, the relation between the value of Mi and c0 is not deterministic. Instead, the probability that a measurement Mi implies an underlying class, cj is given via Bayes' theorem, P(cj|Mi) =P(Mi|cj)P(cj)/P(Mi). The distribution of measurement values, Mi, for each gate dictates the probability P(Mi|cj) and P(cj) scales for the prior probability of each class. The denominator, P(Mi), amounts to a normalization constant. For multiple measurements, M=[M1; M2; . . . ; MN], $$P(c \mid M) = P(M \mid c)P(c)/P(M)$$
$$\approx P(M1 \mid c)P(M2 \mid c) \dots P(MN \mid c)P(c)/P(M)$$

where the approximation made in the second line assumes statistical independence of the measurement features. This assumption is not strictly accurate, but it significantly simplifies the process of determining probability distributions and calculating the probabilities and is commonly applied. If the probability distributions that determine the right hand side of equation 4 can be characterized, each pixel can be classified as the specific gate type, c, that corresponds to the maximum P(c|M). This amounts to dividing the N dimensional measurement space into regions Rj such that M in Rj implies c=cj. Mis-classification errors therefore intuitively result from overlapping probability distributions.

Spatial Sampling

The above-discussed results correspond to an ideal case for classification in which each pixel is perfectly centered at each gate's location. In principle this can be achieved if the gate dimensions in the x-direction share a common factor. This turns out to be the case for the Nangate library used here, but it may not always be true depending on the IC library used. Thus, the effects of sampling and mis-alignment are important to address. In order to gain greater insight into these issues, a series of maps may be generated from a test image, using the previously described training data and feature set.

Figure 11:
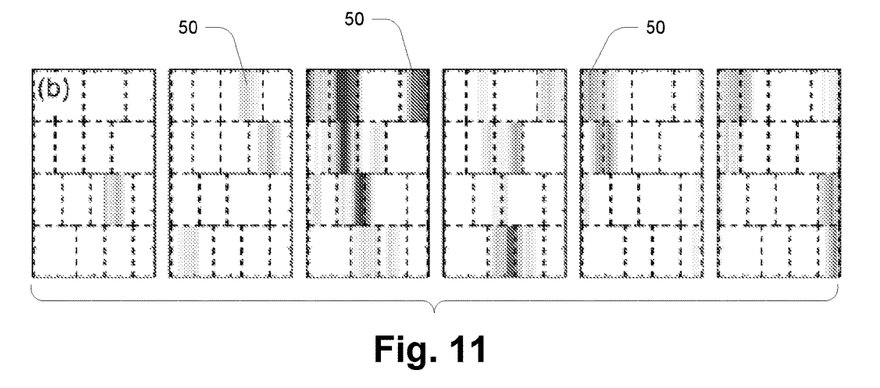
FIG. 11 is a set of spatial gate probability maps for the six gate types.
Figure 12:
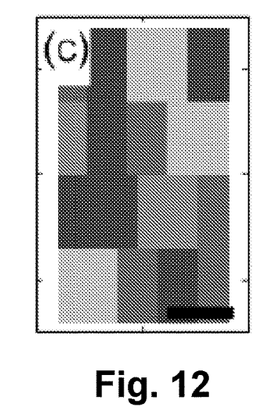
FIG. 12 is a gate map for a simulated test object.
Figure 13:
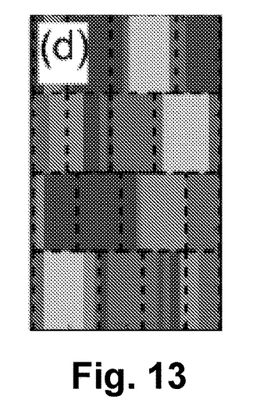
FIG. 13 is a final gate map with each pixel assigned to a gate associated with a maximum probability.

FIGS. 11-13 show gate probability maps and a reconstructed gate level map. FIG. 11 shows spatial maps for the six gates with each pixel shade 50 indicating the probability of a given gate. FIG. 12 is a true (object) spatial map of the gates for the test object, and FIG. 13 is a final gate map determined by assigning each pixel to the gate associated with the maximum probability.

More specifically, FIG. 11 shows the spatial variation of P(cjM) for each gate, with darker color corresponding to higher probability. Comparing these maps with the true gate map shown in FIG. 12, the agreement is excellent. Displaying the probabilities themselves may provide greater insight into sources of error and effects of mis-alignment. In particular, any confusion between similar pairs of gates (e.g., XOR, XNOR) that may be anticipated can be immediately confirmed, especially for both the (AND, OR) and (NAND, NOR) pairs. The correct probabilities in general tend to peak near the center of each gate and also maintain relatively high values (in comparison with the incorrect gates) over the majority of the pixels falling within the gate. This indicates that the classification should be robust to misalignments and should also enable accurate determination of the gates' centers. The final map of FIG. 13, with each pixel classified according to the maximally probable gate, closely matches the true layout, with errors occurring primarily at the boundaries between two different gates as might be expected.

Nanoantenna Labels

As noted above, an additional technique may be used in conjunction with the above-described gate classification technique, i.e., using integrated nanoantenna labels for rapid integrated circuit layout validation. The antenna labeling method acts as an improvement on the gate classification method. Starting with an existing gate library, the goal is generate a new library containing antenna-labeled versions of each of the gate classes, where the antenna-labeled versions can be classified more accurately because of greater distinctiveness of their spectral fingerprints.

Thus disclosed in the concept of integrating optical nanoantennas with IC circuitry in order to selectively label different logic gates. Identifying the gates on the basis of the spectral fingerprints that are engineered with the nanoantenna labels removes the need to image their detailed structure. Similarly, this approach opens the door to mapping the type and location of every logical gate in an integrated circuit in minutes or less with only modest optical resolution.

In the example 45 nm open source library utilized herein, the gates are about 1 mm$^2$ in size and hence can be mapped with a 0.8 NA objective. A statistical pattern recognition approach is used along with an automated screening algorithm to classify the complex spectral fingerprints of the labeled gates and to optimize the antenna labels for maximal accuracy.

The M1 layer in modern ICs is typically copper (Cu), which has optical properties similar to gold, a common plasmonic material. The scale of the dimensions that are present in modern technology nodes are well matched to the sizes of simple wire antennas capable of producing near-IR resonances. In one example, a series of wire shaped antennas suspended in silicon-dioxide (SiO2) 100 nm above a Si substrate are integrated into the M1 layer. The wires are 70 nm wide and have a height of 130 nm, in accordance with the parameters of the Nangate process. Cross sections range from 0.2 to 0.5 um$^2$ on resonance, which are between 12 and 72% of the areas of the smallest variety of a typical 2-input logic gate. The dimensions of the antennas required to support resonances in the near-IR are small enough for them to fit into open space in the M1 layer without having to alter any of the existing electrically functional wires. This includes allowing for adequate separation between structures to satisfy the processes design rules.

Figure 14:
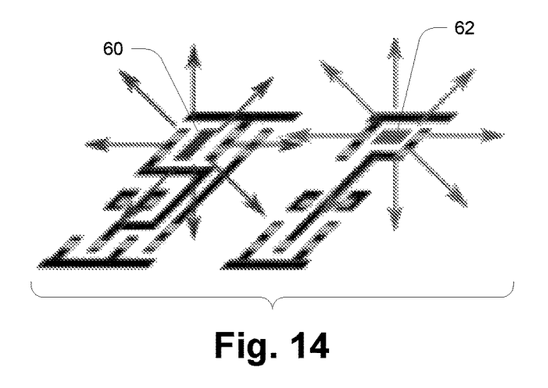
FIG. 14 is an illustration of nanoantenna labels in a pair of gates.

FIG. 14 shows the M1 layers for a pair of standard cells, in this case an OR gate and a NAND gate. Foe each gate, respective antenna labels 60, 62 have been added. The functional metal wires in the IC gates are structurally similar to the adjacent integrated optical antenna. Despite not being explicitly designed to resonantly scatter at well-defined modes in the near-IR, the functional Cu wires are highly polarizable and generate a significant background. This signal interferes coherently with the light scattered from the nanoantenna labels 60, 62 in the far-field. In the near-field the antennas and circuitry couple to each other. As a result the signal from the antenna labeled gates are a complex function of geometry of the antenna itself and the gate into which it is embedded.

For mapping image stacks of labelled ICs to a corresponding gate map, the probabilistic method described above may be utilized. The use of nanoantenna labels tends to better differentiate the probability distributions, making the mapping more accurate. A key observation is that many classification errors result from confusion between specific pairs of gates, such as XNOR and OR for example, that have similar structure. The structural similarity between such pairs of gates can manifest itself in the spectral reflectance. Resulting mis-classification may be especially apparent when only the response to x-polarized incident light is used, and may still dominate when either polarization can be used.

The use of integrated optical nanoantennas provide a means to explicitly tailor the spectral signature of each gate and overcome this critical source of error. The antenna labels may be designed for each gate in an automated fashion, optimizing based on the spectral bandwidth and incident polarization options available for selecting measurement features.

A library of antenna labels can be generated for each gate by defining a set of possible antenna geometries and determining the possible positions for each in the different gates. In one case a series of simple wire antennas such as the ones described previously are used. Their geometries may be determined from all possible combinations of widths and lengths in the sets w in [70; 100] nm and L in [150; 200; 250; 300] nm respectively, as well as oriented in either the x or y direction. The available positions for each antenna in each gate may be automatically determined by exhaustively searching each layout using a fine (e.g., 10 nm) grid. Positions can be ranked and sorted according to uniqueness based on the minimum distance from any preceding locations, and some number (e.g., five) may be kept.

In order to determine optimal combinations of antenna-labeled gates it may be possible to run feature selection and classification routines for different versions of each gate, however, the complex nature of the spectral response of each antenna-labeled gate and the influence on the ability to distinguish between them based on pattern recognition may prevent any simple intuitive design rules. Knowledge of dominant error sources may be used to dramatically reduce the number of combinations to be tested.

Because the majority of errors may result from confusion between certain pairs of gates, a technique may be used of searching for possible combinations of labeled versions of the gates in three stages—one for each of the error prone pairs. This results in a relatively small number of tests.

The steps involved in a testing method may be very similar to those in the gate classification method described above. In the design phase, steps are included for generating and selecting the antenna labeled versions.

Steps Overview

Figure 15:
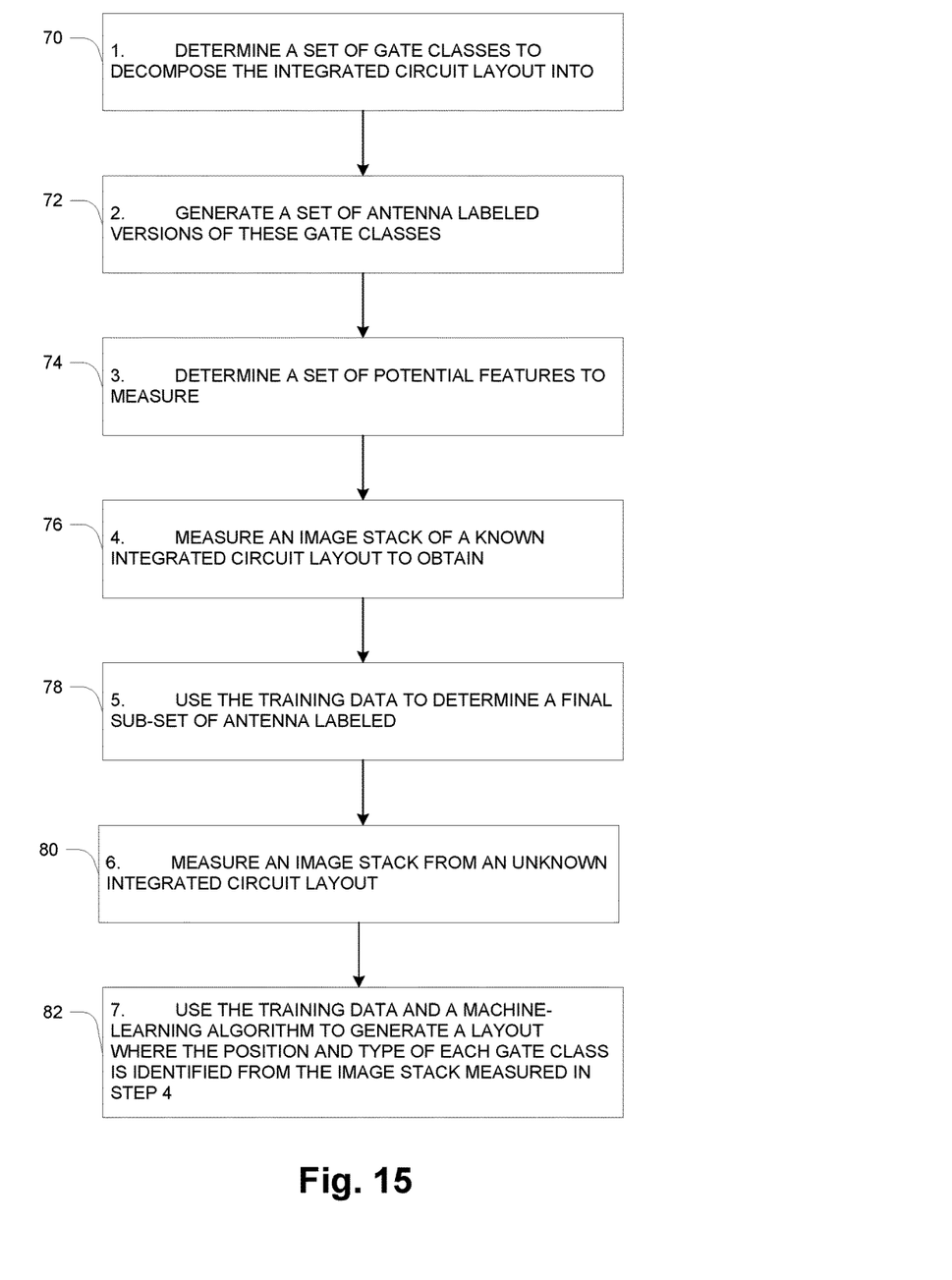
FIG. 15 is a flow diagram of a process of designing, making and testing an IC using nanoantenna labels.

The steps of the process are described with reference to the flow diagram of FIG. 15.

Step 1 (70). Determine a set of gate classes to decompose the integrated circuit layout into.

Step 2 (72). Generate a set of antenna labeled versions of these gate classes.

Step 3 (74). Determine a set of potential features to measure.

Step 4 (76). Measure an image stack of a known integrated circuit layout to obtain training data.

Step 5 (78). Use the training data to determine a final sub-set of antenna labeled versions of the gate classes and a final sub-set of features to measure.

Step 6 (80). Measure an image stack from an unknown integrated circuit layout.

Step 7 (82). Use the training data and a machine-learning algorithm to generate a layout where the position and type of each gate class is identified from the image stack measured in Step 4.

Steps Detail

Step 1. Determine a set of gate classes. This may be the same as in the process for gate classification.

Step 2. Generate a set of antenna labeled versions. For each gate class in the technology library, a series of antenna labeled versions are generated. This is accomplished by adding additional metal or polysilicon lines to the standard. These lines do not have any electrical functionality, but do modify the optical properties of the gate class.

At the end of this step, for an original technology library with N standard cells a new library is obtained with $M_i$ candidate antenna labeled versions for each standard cells (i.e. $M_1$ antenna labeled versions for standard cell 1, $M_2$ antenna labeled versions for standard cell 2, etc.).

Step 3. Determine a set of potential features to measure. This may be the same as in gate classification.

Step 4. Measure an image stack of a known layout to obtain training data. This step is similar to a corresponding step in the gate classification process, but with the following modification. The known layout contains multiple instances of all of the antenna labeled versions of all the standard cells.

Step 5. Use the training data to determine the final sub-set of antenna labeled standard cells and features to measure. The goal is to determine a final set of N antenna labeled versions of the standard cells (1 version of each of the original standard cell types). The training data can be used to assess the performance of all possible combinations of antenna labeled versions in terms of the ability to discriminate between them. Additionally this step can be used to select a subset of features to use for subsequent measurements on unknown circuit layouts.

Step 6. Use the antenna labeled standard cell technology library for subsequent fabrication. This step highlights an important distinction from non-label gate classification methods. In the antenna label method, it is necessary to create a new technology library that contains modified versions of all the standard cells, and then fabricate new chips using this library.

Step 7. Measure an image stack from an unknown integrated circuit layout. Unknown layouts that have been created using the antenna labeled technology library can now be imaged.

Step 8. Generate a layout with the position and type of each gate class. The image stack measured in Step 7 is converted into a layout where the position and type of each gate class are identified.

CONCLUSIONS

Backside spectral imaging of ICs in conjunction with established pattern recognition techniques provides a powerful route towards probing their functionality. The disclosed method can address key obstacles associated with optical resolution and sampling that arise due to the nanoscale features size and massive complexity of modern ICs. These challenges fundamentally limit the ability of traditional imaging techniques to rapidly map a large fraction of a chip. The reduction in resolution requirements we achieve is particularly significant since it overcomes a fundamental physical limitation. Estimates of the trends in gate sizes imply that the approach can easily scale well beyond the nominal "10 nm" technology nodes, where any direct imaging method is completely inconceivable.

The disclosed method may have immediate applicability to the significant problem of ensuring the security of ICs. Other techniques may not offer as direct and informative a measure of the physical layout of a fabricated IC in a rapid and non-destructive fashion. The information obtained can be used to directly verify the IC layout and spatially localize suspicious regions. The technique may also be used in conjunction with other techniques to encode optical watermarks in an IC layout for even greater accuracy and speed.

While this description focuses on utilizing spectral fingerprints to distinguish between different IC gates here, the sensitivity of the spectral scattering response to nanoscale structure points to the opportunity to obtain more detailed information. For example, it is well known that forming conductive bridges in nanoscale metallic structures dramatically alters their antenna-like characteristics. The disclosed technique may be applied to detecting bridging defects which are becoming increasingly significant as a result of increased wire density. This is relevant to failure analysis where related concepts of leveraging prior information to improve spatial resolution are beginning to be explored.

In general, ICs represent a compelling and ideal application of the spectral fingerprinting methods described herein. They are inherently modular since their design paradigm is based on abstraction, hence their components fit neatly into a few well defined classes. Their physical structures are also highly uniform—an enormous amount of effort is applied to ensure this on the fabrication end in order to provide adequate yield. This implies that in physical measurements sample variations will be minimized. Both of these are dramatic departures and improvements over the situations where spectroscopic imaging techniques are often applied such as in biological systems. Access to sufficient and representative samples to use as training data is a final critical need in classification techniques that ICs offer perhaps better than any other physical system. A single IC contains typically over a million gates that are repeated and reused through-out multiple chips on multiple fabrication runs. Measurements on a small fraction of a single chip can supply training data that can be used in a classification method that will be applied to millions of chips. Spectroscopic imaging techniques therefore have the potential to satisfy critical metrology needs, in security and also general applications, that are increasingly significant as the feature sizes and complexity in modern ICs passes beyond what can be addressed with traditional tools.

Possible Variations

The following are ways in which certain specifics described herein may be generalized to enable use of the technique in similar or different applications.

A. For Gate Classification:

1. The unit of identification need not be limited to a single cell or gate. The concepts can be extended to any modular subunit in an IC, including common groups of cells, regular arrays such as registers and memory arrays, etc.

2. The spectral fingerprint need not be restricted to a response to different incident wavelength and polarization combinations. It can include angular spectrum, polarization rotation, incident spot geometry etc. Generally any technique involving reflection microscopy may be used. Also, broadband illumination may be used instead of discrete narrow-band illumination.

3. The illumination may be varied (e.g. focused beam, Kohler, structured).

4. The processing need not be restricted to training-based Bayesian classification. Generally any machine-learning technique may be used.

5. The electrically functional elements may be specifically tailored to produce unique optical signatures. This might be done using certain geometrical layout techniques that enhance distinctness in the optical identification process, and/or incorporation of additional elements that provide enhancements (e.g., optical antennas).

B. For Nanoantenna Labels:

1. It is possible that not every standard cell in the technology library needs be modified with an antenna.

2. The functional electronic elements of the standard cells could be altered as well, still preserving the core electronic functionality but with a different layout that accommodates better or larger antenna labels or itself gives rise to a more unique signature.

3. A set of intuitive rules could be developed for selecting optimal antenna labeled versions of the gate classes without having to perform the selection in Step 5.

While various embodiments of the invention have been particularly shown and described, it will be understood by those skilled in the art that various changes in form and details may be made therein without departing from the scope of the invention as defined by the appended claims.

What is claimed is:

1. A method of optical verification testing of a portion of an integrated circuit, comprising:
   (a) obtaining one or more images of the portion of the integrated circuit by, for each image:
      (i) illuminating the integrated circuit with excitation light, wherein the excitation light corresponds to a respective specific optical excitation of a predefined spectrum of optical excitations; and
      (ii) detecting scattered light from the integrated circuit in response to the specific optical excitation; and
   (b) for each of a plurality of sub-regions of the images, mapping the respective sub-region to at least one of (i) a specific sub-unit of a predefined set of sub-units of the integrated circuit and (ii) a null result, based on an intensity of one or more pixels within the sub-regions of the one or more images, wherein for each image, the intensity of the pixels corresponds to an intensity of detected scattered light from a corresponding region of the portion of the integrated circuit in response to the respective specific optical excitation, thereby creating a representation of a detected layout of the integrated circuit as an arrangement of the sub-units.

2. The method of claim 1, wherein illuminating the integrated circuit includes using a broadband optical source generating broadband illumination across the spectrum of optical excitations, and wherein detecting scattered light from the integrated circuit includes using filters for detecting respective responses to the optical excitations occurring simultaneously in response to the broadband illumination.

3. The method of claim 1, wherein illuminating the integrated circuit includes using a series of narrowband sources each providing a corresponding distinct one of the optical excitations, and wherein detecting scattered light from the integrated circuit includes multiple distinct detections each occurring when a corresponding distinct optical excitation is provided.

4. The method of claim 1, wherein the predefined spectrum of optical excitations includes a wavelength spectrum.

5. The method of claim 4, wherein the predefined spectrum of optical excitations further includes a set of polarizations used in combination with wavelengths of the wavelength spectrum.

6. The method of claim 1, wherein the predefined spectrum of optical excitations includes a set of polarizations.

7. The method of claim 1, wherein mapping the sub-regions includes use of a machine learning technique.

8. The method of claim 7, wherein the machine learning technique is a training-based Bayesian technique providing estimates of probabilities used to map the sub-regions to respective sub-units.

9. The method of claim 1, wherein the predefined set of sub-units are gates.

10. The method of claim 1, wherein the predefined set of sub-units are antenna-labeled versions of a corresponding set of non-labeled sub-units from which the antenna-labeled version are created by addition of antenna structure for enhancing distinctness of optical response.

11. The method of claim 1, used in verifying a detected layout of a fabricated integrated circuit to a designed layout for a design of the fabricated integrated circuit, and further including comparing the representation of the detected layout to a separate representation of the designed layout to detect deviation of the detected layout from the designed layout.

12. An integrated circuit comprising a plurality of antenna-labelled sub-units being antenna-labeled versions of a corresponding set of non-labeled sub-units from which the antenna-labeled version are created by addition of antenna structure for enhancing distinctness of optical response.

* * * * *